US00PP23459P2

(12) United States Plant Patent

Stewart et al.

(10) Patent No.: US PP23,459 P2

(45) Date of Patent: Mar. 12, 2013

(54) STRAWBERRY PLANT NAMED 'DRISSTRAWTWENTYEIGHT'

(50) Latin Name: *Fragaria×ananassa*
Varietal Denomination: DrisStrawTwentyEight

(75) Inventors: Philip J. Stewart, Watsonville, CA (US); Joanne F. Coss, Pebble Beach, CA (US); Martin P. Madesko, Aptos, CA (US); Bruce D. Mowrey, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 13/373,119

(22) Filed: Nov. 4, 2011

(51) Int. Cl.
*A01H 5/00* (2006.01)

(52) U.S. Cl. ..... Plt./209

(58) Field of Classification Search ..... Plt./208
See application file for complete search history.

*Primary Examiner* — Annette Para

(74) *Attorney, Agent, or Firm* — Jondle & Associates, P.C.

(57) ABSTRACT

A new and distinct variety of strawberry plant named 'DrisStrawTwentyEight' characterized by having medium sized, conical fruit with medium sweetness and high yield is disclosed.

3 Drawing Sheets

Genus and species: *Fragaria×ananassa.*
Variety denomination: 'DrisStrawTwentyEight'.

BACKGROUND OF THE NEW PLANT

The present invention relates to a new and distinct strawberry variety designated 'DrisStrawTwentyEight' and botanically known as *Fragaria×ananassa*. This new strawberry variety was discovered in Monterey County, Calif. in July 2007 and originated from a cross between the proprietary female parent '95L299' (unpatented) and the proprietary male parent '251M27' (unpatented). A single plant was selected for asexual propagation via tissue culture and vegetative cuttings in Shasta County, Calif. in 2007.

'DrisStrawTwentyEight' underwent further testing in Monterey County, Calif. for five years (2007-2011). The present invention has been found to retain its distinctive characteristics through successive asexual propagations via stolons and tissue culture.

Plant Breeder's Rights for this variety have not been applied for. 'DrisStrawTwentyEight' has not been made publicly available or sold more than one year prior to the filing date of this application.

SUMMARY OF THE INVENTION

The following are the most outstanding and distinguishing characteristics of this new cultivar when grown under normal horticultural practices in Monterey County, Calif.

1. High yield;
2. Medium sized, conic shaped fruit; and
3. Medium sweetness.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from eight-month-old plants.

DESCRIPTION OF THE NEW VARIETY

Figure 1:
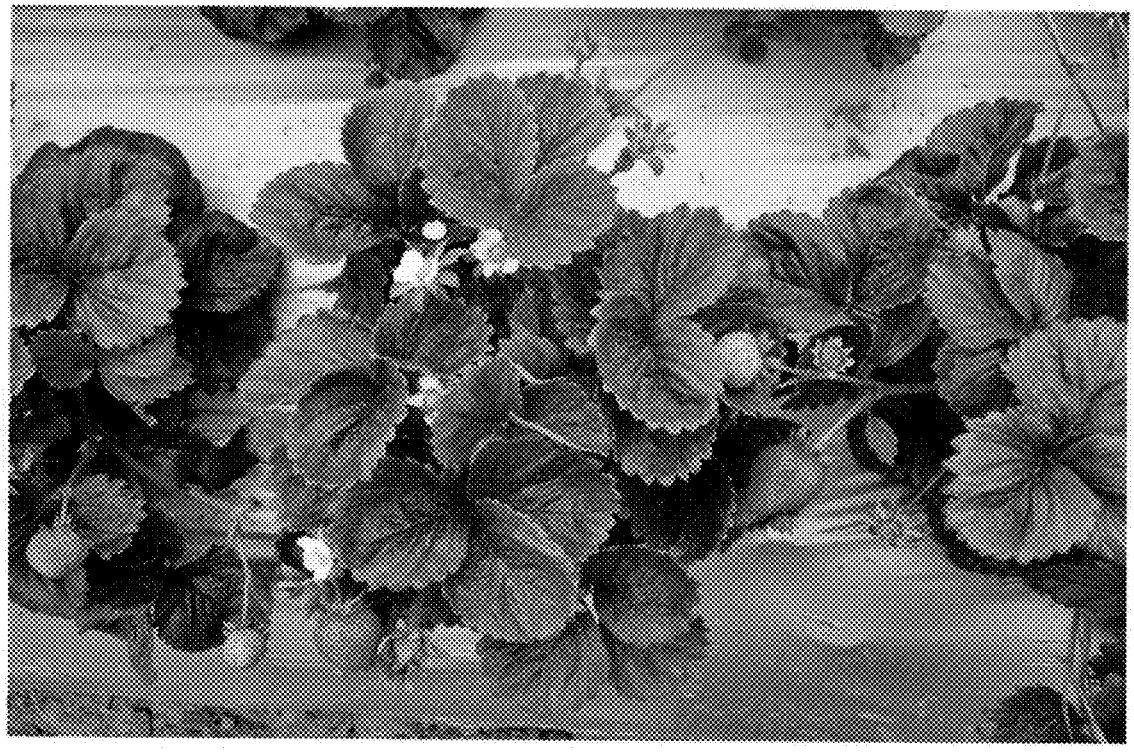
FIG. 1 shows overall plant habit including fruit at various stages of development.
Figure 2:
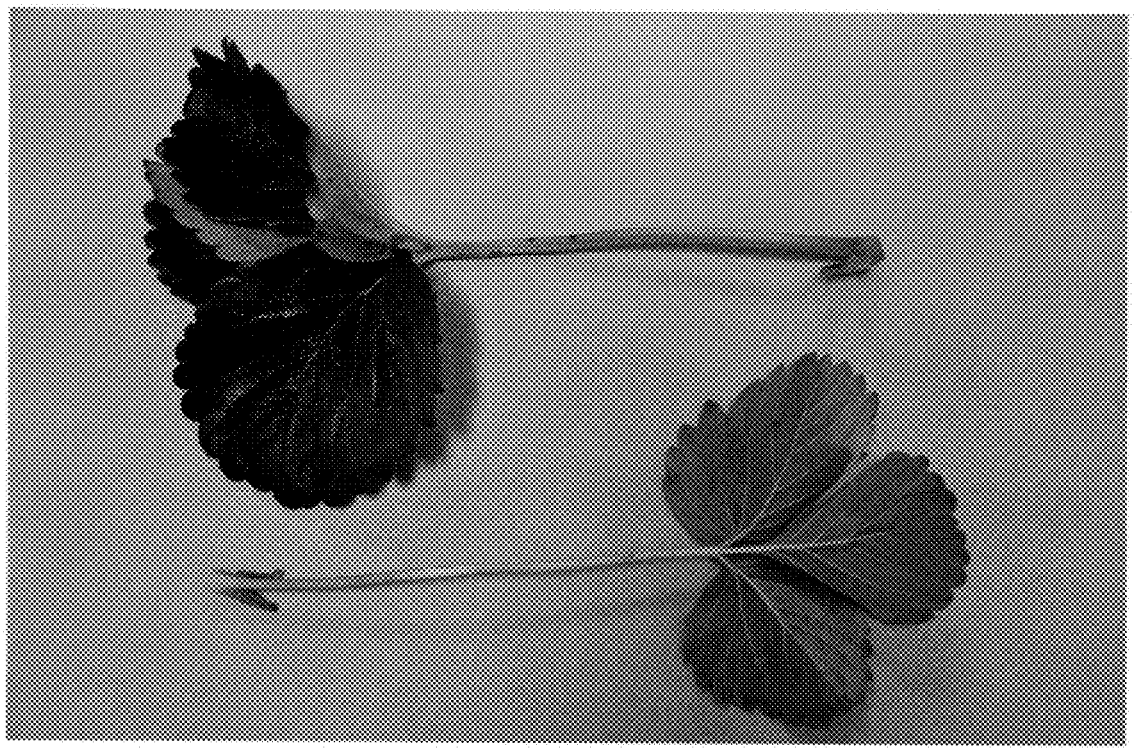
FIG. 2 shows upper and lower surfaces of the leaves of the plant with three leaflets.
Figure 3:
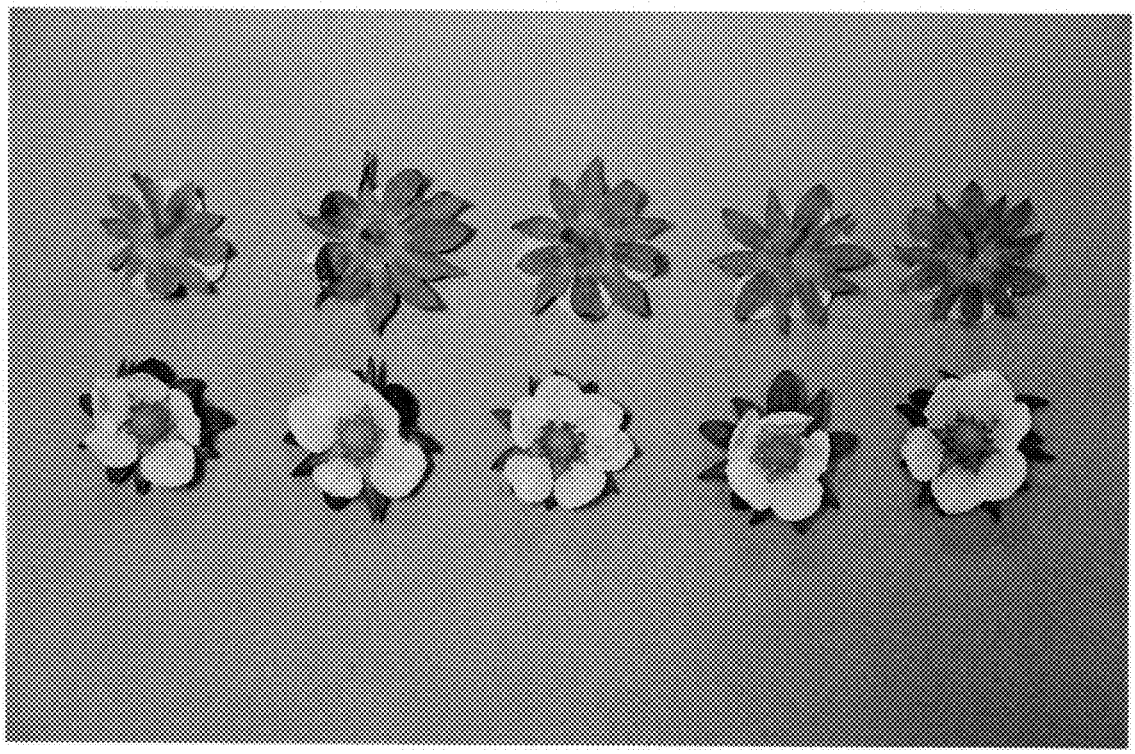
FIG. 3 shows both upper and lower surfaces of the flowers.
Figure 4:
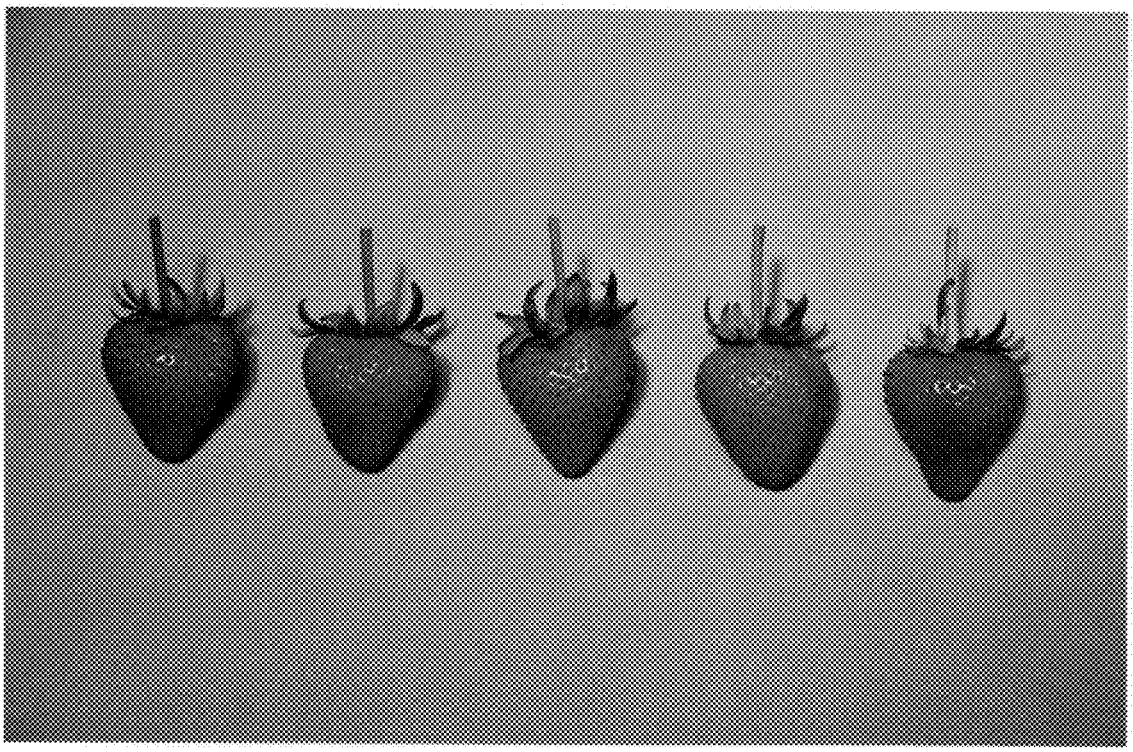
FIG. 4 shows the whole fruit.
Figure 5:
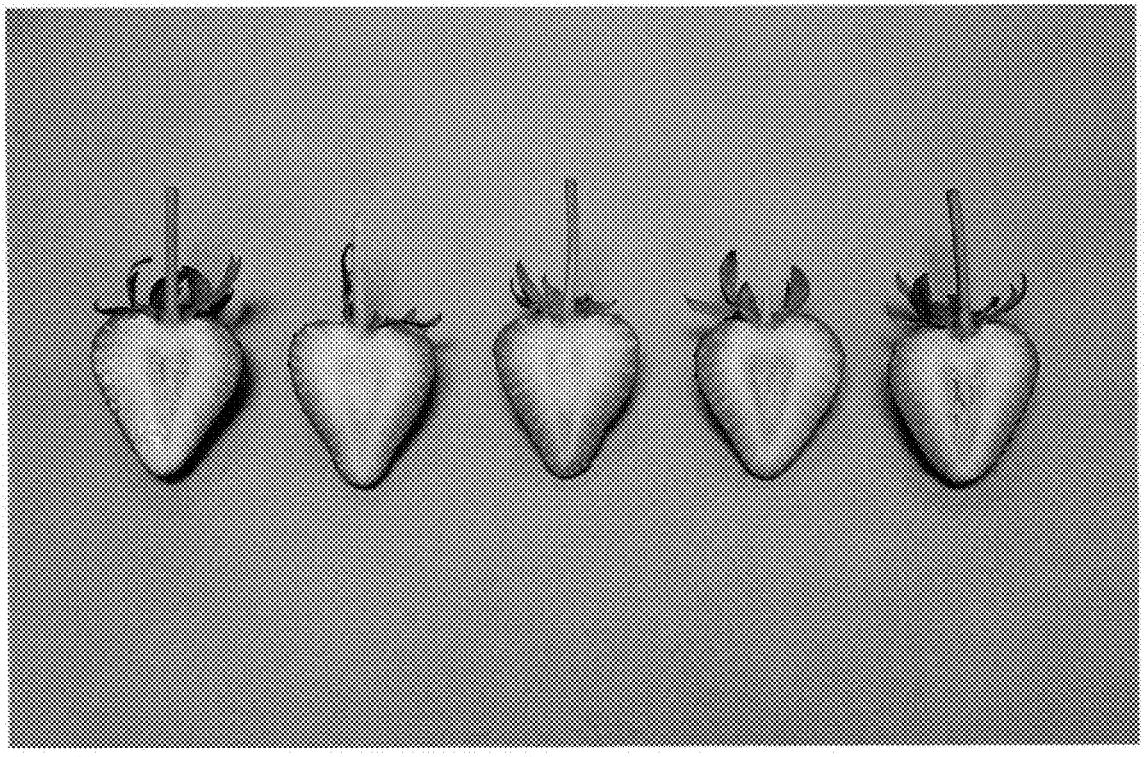
FIG. 5 shows the fruit in longitudinal cross-section.

The following detailed descriptions set forth the distinctive characteristics of 'DrisStrawTwentyEight'. The data which define these characteristics is based on observations taken in Monterey County, Calif. from 2007 to 2011. This description is in accordance with UPOV terminology. Color designations, color descriptions, and other phenotypical descriptions may deviate from the stated values and descriptions depending upon variation in environmental, seasonal, climatic, and cultural conditions. 'DrisStrawTwentyEight' has not been observed under all possible environmental conditions. The botanical description of 'DrisStrawTwentyEight' was taken from eight-month-old plants. Color references are primarily to The R.H.S. Colour Chart of The Royal Horticultural Society of London (R.H.S.) (2001 edition). Descriptive terminology follows the *Plant Identification Terminology, An Illustrated Glossary,* $2^{nd}$ edition by James G. Harris and Melinda Woolf Harris, unless where otherwise defined.

DETAILED BOTANICAL DESCRIPTION OF THE PLANT

Classification:

*Species.*—*Fragaria×ananassa.*
*Common name.*—Strawberry.
*Denomination.*—'DrisStrawTwentyEight'.

Parentage:

*Female parent.*—The proprietary variety '95L299' (unpatented).
*Male parent.*—The proprietary variety '251M27' (unpatented).

Plant:
*Height*.—25.3 cm.
*Diameter*.—43.3 cm.
*Number of crowns/plant*.—3.
*Habit*.—Flat globose.
*Density of individual plant*.—Medium.
*Vigor* (*health and hardiness of plant*).—Strong.

Terminal leaflets:
*Size*.—Small. Length: 7.7 cm. Width: 7.8 cm. Length/width ratio: 1.0 (As long as broad).
*Number of teeth/terminal leaflet*.—20.
*Shape of teeth*.—Rounded-crenate.
*Color*.—Upper surface: RHS 147A (Dark yellow-green). Lower surface: RHS 148C (Medium yellow-green).
*Shape in cross section*.—Concave.
*Blistering*.—Medium.
*Glossiness*.—Medium.
*Number of leaflets*.—Three only.
*Shape*.—Orbicular.
*Base shape*.—Rounded.
*Apex descriptor*.—Rounded.
*Variegation*.—Absent.
*Margin*.—Crenate.
*Margin profile*.—Revolute (margins rolled backwards).

Petiole:
*Length*.—16.0 cm.
*Diameter*.—3.32 mm.
*Pubescence*.—Sparse.
*Pose of hairs*.—Outwards-horizontal.
*Color*.—RHS 145A (Medium yellow-green).

Petiolule:
*Length*.—10.02 mm.
*Diameter*.—1.53 mm.
*Bract frequency*.—1.
*Color*.—RHS 145A (Medium yellow-green).

Stipule:
*Length*.—3.4 cm.
*Width*.—9.11 mm.
*Pubescence*.—Dense.
*Stipule anthocyanin coloration*.—Weak; RHS 52B (Medium red).

Stolon:
*Number*.—Medium.
*Average number of daughter plants per plant*.—49.
*Stolon anthocyanin*.—Medium; RHS 41B (Medium red).
*Thickness*.—Medium.
*Pubescence*.—Medium.

Inflorescence:
*Position relative to foliage*.—Level.
*Number of flowers*.—Medium.
*Time of flowering* (50% *of plants at first flower*).—Early to medium.
*Flower size*.—Small.
*Diameter*.—27.98 mm.
*Petals*.—Shape: Orbicular. Apex: Rounded. Base: Concavo-convex. Margin: Entire. Spacing: Overlapping. Length: 12.01 mm. Width: 11.98 mm. Length/width ratio: 1.0 (As long as broad). Typical and observed petal number per flower: 6. Color (upper surface): RHS 155C (White).
*Calyx*.—Diameter: 31.98 mm. Diameter relative to corolla: Larger. Inner calyx diameter relative to outer: Same size. Insertion of calyx: Level. Pose of calyx segments: Reflexed-upwards. Size of calyx in relation to fruit: Same size. Adherence of calyx: Weak.
*Sepal*.—Shape: Oval. Apex: Convex. Margin: Entire. Length: 12.28 mm. Width: 5.53 mm. Typical and observed sepal number per flower: 10 or 12.
*Receptacle color*.—RHS 6A (Medium yellow).
*Stamen*.—Present. Anther color: RHS 166A (Dark greyed-orange).
*Pedicel*.—Attitude of hairs: Upwards.

Fruiting truss:
*Length*.—Long; 23.4 cm.
*Diameter at base of truss*.—4.19 mm.
*Number of berries per fruiting truss*.—4.
*Attitude at first picking*.—Prostrate.
*Color at base of truss*.—RHS 145B (Medium yellow-green).

Fruit:
*Relative fruit size*.—Medium.
*Length*.—44.01 mm.
*Width*.—39.78 mm.
*Length/width ratio*.—1.1 (As long as broad).
*Fruit hollow length*.—11.17 mm.
*Fruit hollow width*.—3.55 mm.
*Fruit hollow length/width ratio*.—3.1 (Longer than broad).
*Fruit hollow center* (*cavity*).—Small.
*Weight* (*per individual berry*).—21.1 g.
*Predominant fruit shape*.—Conical.
*Difference in shape between primary and secondary fruits*.—None or very slight.
*Evenness of fruit surface*.—Even or very slightly uneven.
*Fruit skin color*.—RHS 46A (Dark red).
*Evenness of fruit color*.—Even or very slightly uneven.
*Fruit glossiness*.—Medium.
*Achenes*.—Insertion of achenes: Above surface. Coloration (sunward side of berry): RHS 178B (Dark greyed-red). Coloration (shaded side of berry): RHS N144B (Medium yellow-green). Number per berry: 272. Weight (weight achenes divided by total # seed): 0.000581324. Width of band without achenes: Medium.
*Firmness of flesh*.—Firm.
*Color of flesh* (*excluding core*).—RHS 43B (Medium red) and RHS 155B (White).
*Color of core*.—RHS 43D (Light red) and RHS 49B (Light red).
*Evenness of flesh color*.—Even.
*Distribution of flesh color*.—Marginal and central.
*Sweetness*.—Medium.
*Acidity*.—Strong.
*Texture when tasted*.—Medium.
*Type of bearing*.—Partially everbearing-partially remontant.
*Grams of fruit/plant*.—1218.0 g.
*Harvest interval*.—April-November.
*Harvest maturity*.—Mid-season.

Disease, pest, and stress resistance:
*Botrytis fruit rot*.—Resistant to moderately resistant.
*Powdery mildew*.—Moderately susceptible.
*Verticillium wilt*.—Moderately susceptible.
*High temperatures*.—Moderately susceptible.
*Wind*.—Moderately susceptible to susceptible.

COMPARISON WITH PARENTAL AND COMMERCIAL VARIETIES

When 'DrisStrawTwentyEight' is compared to the proprietary female parent '95L299' (unpatented), 'DrisStrawTwentyEight' is higher yielding and has larger fruit than '95L299'.

When 'DrisStrawTwentyEight' is compared to the proprietary male parent '251M27' (unpatented), 'DrisStrawTwentyEight' has better shelf life, better flavor and better yields than '251M27'.

When 'DrisStrawTwentyEight' is compared to the commercial variety 'San Juan' (U.S. Plant Pat. No. 12,899), 'DrisStrawTwentyEight' has strong plant vigor, a concave leaf shape in cross section and only three leaflets, while 'San Juan' has medium plant vigor, a flat to slightly convex leaf shape in cross section, and sometimes more than three leaflets. Additionally, 'DrisStrawTwentyEight' has a long fruiting truss, and fruit with a medium sized band without achenes and small hollow center, while 'San Juan' has a medium length fruiting truss, and fruit with a narrow band without achenes and a medium sized hollow center.

When 'DrisStrawTwentyEight' is compared to the commercial variety 'DrisStrawNine' (U.S. Plant Pat. No. 20,733), 'DrisStrawTwentyEight' has a flat globose habit with strong vigor, and terminal leaflets with crenate margins, while 'DrisStrawNine' has an upright habit with weak vigor, and terminal leaflets with flat margins. Additionally, 'DrisStrawTwentyEight' has a long fruiting truss with a prostate attitude on a partially everbearing plant, while 'DrisStrawNine' has a medium length fruiting truss with a semi-erect attitude on a fully everbearing plant.

We claim:

1. A new and distinct variety of strawberry plant named 'DrisStrawTwentyEight' as described and shown herein.

* * * * *